(12) United States Patent
Liechty et al.

(10) Patent No.: US 7,461,987 B2
(45) Date of Patent: Dec. 9, 2008

(54) DEVICE FOR PACKAGING AND DISTRIBUTING AT LEAST TWO DIFFERENT COMPONENTS, ASSEMBLY INCLUDING SUCH A DEVICE, AND PROCESS USING SUCH A DEVICE

(75) Inventors: Anne Liechty, Paris (FR); Anke Hadasch, Paris (FR)

(73) Assignee: **L*Oreal**, Paris (FR)

( * ) Notice: Subject to any disclaimer, the term of this patent is extended or adjusted under 35 U.S.C. 154(b) by 624 days.

(21) Appl. No.: 11/272,715

(22) Filed: Nov. 15, 2005

(65) Prior Publication Data

US 2006/0108247 A1  May 25, 2006

Related U.S. Application Data

(60) Provisional application No. 60/630,302, filed on Nov. 24, 2004.

(30) Foreign Application Priority Data

Nov. 15, 2004  (FR) .................................. 04 52620

(51) Int. Cl.
*A46B 11/00* (2006.01)
*B67D 5/56* (2006.01)

(52) U.S. Cl. ..................... 401/47; 401/44; 401/205; 222/129; 222/134; 222/144.5

(58) Field of Classification Search ............ 401/44–47, 401/205, 198; 222/136, 129, 134, 144.5, 222/14.6, 145.75; 132/317
See application file for complete search history.

(56) References Cited

U.S. PATENT DOCUMENTS

| 2,136,204 | A | * | 11/1938 | Amdur | ......................... 401/17 |
| 5,111,972 | A | | 5/1992 | Sakurai et al. | |
| 6,116,466 | A | | 9/2000 | Gueret | |
| 6,357,450 | B1 | | 3/2002 | Paice | |
| 6,505,983 | B1 | * | 1/2003 | Seo | ............................ 401/47 |
| 2004/0221864 | A1 | | 11/2004 | Capristo | |

* cited by examiner

*Primary Examiner*—David J Walczak
(74) *Attorney, Agent, or Firm*—Oliff & Berridge, PLC

(57) ABSTRACT

A device for packaging and distributing at least first and second cosmetic compositions, which are different from each other and which may be mixed together for the purpose of applying them to keratin materials may be configured to separately store the first and second compositions. The device may include a regulating member configured to allow a user to vary a relative proportion of at least one composition in the mixture, the relative proportion conditioning at least one visible optical effect other than color in the mixture.

56 Claims, 2 Drawing Sheets

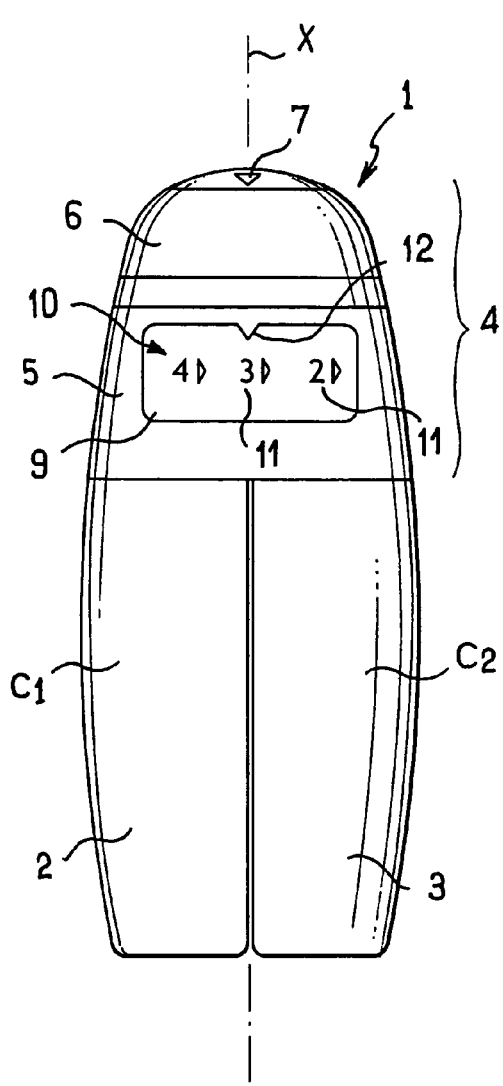
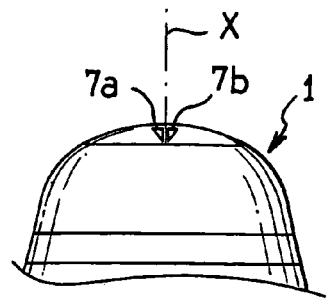
FIG.2
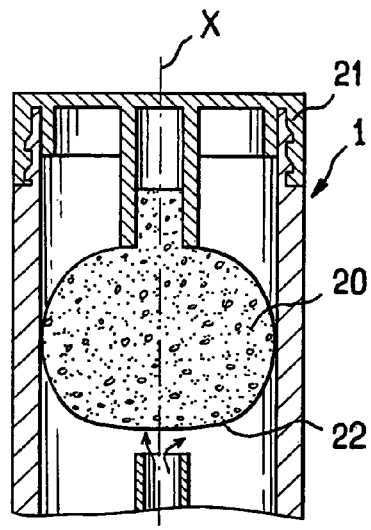
FIG.3
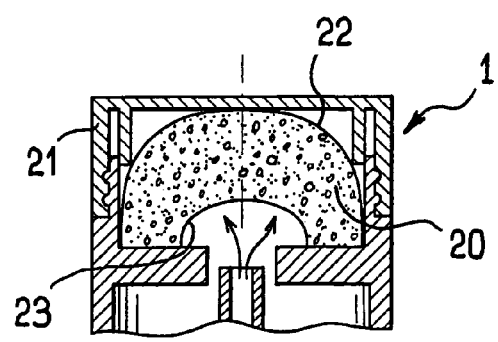
FIG.4
FIG.1

DEVICE FOR PACKAGING AND DISTRIBUTING AT LEAST TWO DIFFERENT COMPONENTS, ASSEMBLY INCLUDING SUCH A DEVICE, AND PROCESS USING SUCH A DEVICE

CROSS-REFERENCE TO RELATED APPLICATIONS

This non-provisional application claims the benefit of French Application No. 04 52620 filed on Nov. 15, 2004, and U.S. Provisional Application No. 60/630,302 filed on Nov. 24, 2004, the entire disclosures of which are incorporated herein by reference.

The present invention relates to devices for packaging and distributing at least two different compositions, especially cosmetics, which are stored separately and which may be mixed together during use. In particular, the compositions may be distributed by such devices for applying them to a keratin material such as skin, mucous membranes or integuments.

BACKGROUND

European patent EP 0 758 615 describes a device for placing, in the same packaging, several products with different sun protection factors or an antisun product and an after-sun product such as a moisturizing cream.

Other devices for packaging two products in separate containers and for varying proportions of the products in an applied mixture are known, especially from European patent applications EP 0 427 609, EP 1 040 773, U.S. Pat. No. 5,971,210 or U.S. Pat. No. 4,893,729.

The company Versadial Martkoberdorf proposes a device for distributing a mixture of two different antisun products stored separately. The proposed device comprises a regulating member that enables a user to select a relative proportion of each product in the mixture.

U.S. Pat. No. 5,013,244 describes a kit comprising a first device storing and distributing a first antisun product with a low protection factor and a second device storing and distributing a colored second antisun product with a high protection factor. The kit comprises a colorimetric scale giving information regarding the sun protection factor obtained according to the color of the mixture of the two products, which a user can prepare in his hand. The colorimetric scale is not intended to be representative of the color of the mixture after application to the skin.

SUMMARY

There is a need to be able to benefit from novel devices for packaging and distributing cosmetic products.

The invention is especially directed toward satisfying this need.

Exemplary embodiments of the present invention may provide a device for packaging and distributing at least first and second compositions, especially cosmetic compositions, which are different from each other and which may be mixed together for the purpose of applying them to keratin materials, the device being configured to separately store the first and second compositions and comprising a regulating member allowing a user to vary the relative proportion of at least one composition in the obtained mixture, the relative proportion conditioning at least one visible optical effect other than the color in the obtained mixture.

The term "visible optical effect" denotes an optical effect that may be observed by the naked eye. The relative proportion may be capable, where appropriate or desired, of also conditioning a color variation in the obtained mixture. The second composition may be capable, where appropriate or desired, also of affording a color variation in the obtained mixture.

In exemplary embodiments, the second composition is configured to producing the optical effect with a variable degree, especially with varying degrees perceptible by the human eye, as a function of its proportion in the mixture.

In exemplary embodiments, the second composition may comprise, for example, at least one material, especially particles, or a phase, that contribute partially or totally toward the production of the visible optical effect other than the color.

In such exemplary embodiments, the user may vary at will at least one optical effect other than the color, produced by the mixing of the two compositions that he will apply to skin or mucous membranes, especially lips, or alternatively integuments, for example, nails, eyelashes or hair.

In exemplary embodiments, the user may especially adapt the optical effect as a function of his attire, the time of the day, the weather or the season, the occasion or alternatively his mood or the area made up with the product.

In exemplary embodiments, the device may optionally serve several users, for example, within a family, each user being able to select the makeup result that best suits him.

In exemplary embodiments, the two compositions that are combined in the device may advantageously include a same galenical form or compatible galenical forms. This may enable a user to combine a composition such as a foundation or a moisturizing composition with a composition providing, for example, an optical effect other than the color, without any worry regarding the incompatibility of galenical forms, which may be the case for several compositions packaged in different devices, or even sold by different companies.

In exemplary embodiments, the optical effect other than the color may be, for example, coverage, variation of color as a function of angle of observation, diffraction of light, inhomogeneity of appearance of the mixture, gloss or matteness, this list not being limiting.

In exemplary embodiments, the first composition may be configured to provide at least one visible optical effect, for example, by a material that it comprises.

In exemplary embodiments, at least one of the first and second compositions may be free of coloring agent. In exemplary embodiments, at least one of the first and second compositions may comprise at least one coloring agent.

In exemplary embodiments, the first composition and the second composition may each comprise at least one coloring agent, for example the same coloring agent, in different or equal concentrations.

In exemplary embodiments, the coloring agent(s) contained in one or in both compositions may be selected from mineral pigments, organic pigments and lakes, nacreous pigments, composite pigments and liposoluble or water-soluble dyes, and mixtures thereof.

In exemplary embodiments in which the first and second compositions each comprise several pigments, relative proportions of the pigments among each other within each composition may be substantially the same, so as, for example, to make it possible to vary coverage without substantially varying the color when the proportion of the second composition in the mixture varies.

In exemplary embodiments in which the optical effect comprises coverage or mattness, the second composition may comprise at least one pigment or filler, especially a filler that may be selected from talc, mica, silica, kaolin, sericite, polyamide powder, polyolefin powder, polyethylene powder, polytetrafluoroethylene powder, polymethyl methacrylate powder, polyurethane powder, starch powder and silicone resin beads.

In exemplary embodiments in which the optical effect comprises a variation in color as a function of an angle of observation, the second composition may comprise at least one goniochromatic coloring selected, for example, from interference multilayer structures and liquid-crystal coloring agents.

In exemplary embodiments in which the optical effect comprises diffraction of light, the second composition may comprise at least one diffractive pigment.

In exemplary embodiments in which the optical effect comprises inhomogeneity of the appearance of the mixture, the second composition may comprise colored or reflective particles, which are visible to the naked eye, for example, flakes or fibers.

In exemplary embodiments in which the optical effect comprises gloss, the second composition may comprise, for example, reflective particles, nacres or metal-coated particles, and/or a glossy oily phase depending, for example, on the galenical form or the intended use of the mixture.

In exemplary embodiments, the first and second compositions may be free of UV-screening agent. As used herein, the term "UV-screening agent" means a material including an absorption spectrum mainly in the UVA and/or UVB range.

In exemplary embodiments, the first composition may, for example, be free of coloring agent and may constitute a "neutral base", which may be white or transparent, and the second composition may comprise, for example, at least one nacre, at least one coloring agent and a nacre, or alternatively at least one filler and a coloring agent, or alternatively at least one goniochromatic coloring agent, or a mixture thereof. In exemplary embodiments, the first composition may comprise a coloring agent and the second composition may comprise a nacre and/or a filler, or alternatively reflective particles, or a mixture thereof.

In exemplary embodiments, the device may be combined with a plurality of different compositions, for example, of different colors, that may be used as first composition. In exemplary embodiments, the device may also be combined with a plurality of different compositions that may be used as second composition.

In exemplary embodiments, the first and second compositions may be cosmetic compositions, including care compositions, especially intended to be applied to keratin materials, for example, skin, mucous membranes, especially lips, or integuments, especially nails or keratin fibers. The expression "cosmetic composition" covers compositions as defined in Directive 93/35/EEC of the Council of 14 Jun. 1993. The first and second compositions in various exemplary embodiments comprise a physiologically acceptable medium. The term "physiologically acceptable medium" denotes a non-toxic medium that may be applied to human skin, lips or integuments. The physiologically acceptable medium may be adapted to the nature of the support onto which the mixture is intended to be applied, and also to the form in which the compositions are intended to be packaged, for example, fluid at room temperature and at atmospheric pressure.

Modes of Mixing

In exemplary embodiments, the mixing of the first and second compositions may be performed inside the device, or, alternatively, the first and second compositions may be distributed separately, and may or may not be mixed outside the device.

In exemplary embodiments in which the mixing is performed inside the device, the device may comprise a mixing chamber. The chamber may comprise a stirrer and/or channels configured to facilitate the mixing of the compositions.

In exemplary embodiments in which the mixing is performed outside the device, the mixing may take place in situ, in the palm of the hand or in a dish, for example.

In exemplary embodiments, the device may be configured so as to be able to simultaneously or successively distribute the first and second compositions.

Regulating Member

In exemplary embodiments, the regulating member of the device may be rotary or non-rotary; the term "regulating member" should not be understood as being limiting. In exemplary embodiments, the regulating member may include a mechanism comprising several interacting components. In exemplary embodiments, the regulating member may be, where appropriate or desired, dual, with, for example, two regulating components that may be operated independently of each other and that act respectively on the amounts of each composition that are distributed.

Especially in exemplary embodiments in which the regulating member is single, the device may comprise at least two positions corresponding to different relative proportions of first composition and of second composition in the mixture.

In exemplary embodiments, the regulating member may be configured so as to allow, for example, in extreme positions, the user to distribute one of the compositions alone, or alternatively one or other of the compositions alone.

In exemplary embodiments, the regulating member may be configured to allow continuous setting of the proportion of one of the compositions in the mixture, so as to vary its proportion, for example between 0% and 100% at the user's discretion. Alternatively, the regulating member may be configured to allow a setting in increments of the proportion of one of the compositions in the mixture, for example between 0% and 100%, at the user's discretion, and may comprise at least two separate regulating positions, or even three or four or advantageously more positions, each position corresponding to a mixture comprising a predetermined proportion of second composition. In exemplary embodiments, the regulating member may be configured to emit a click or to have a hard point for each position to facilitate its positioning by the user in a given position.

In exemplary embodiments, a course of the regulating member between two successive positions may represent, for example, less than a quarter of a total course, between two extreme positions of the regulating member.

In exemplary embodiments, the regulating member may be configured, for example, to make it possible to obtain after distribution a mixture containing, for a first position of the regulating member, for example, between 0% and 50% by weight of the second composition relative to the total weight of the mixture, and for a final position of the regulating member, for example, between 50% and 100% by weight of the second composition.

For example, a given position of the regulating member may make it possible to obtain a mixture containing 90% of the first composition and 10% of second composition. If the user wishes the optical effect to be different, he may select a position of the regulating member that will produce a mixture containing more of second composition, for example, 20% or 30% by weight, or even more.

In exemplary embodiments, the device may comprise a single press-button to distribute the mixture or an independent press-button for the distribution of each composition. In exemplary embodiments, the press-button(s) may act on pumps or valves, for example.

In exemplary embodiments, the device may be configured, for example, so that the modification of the coverage or of the homogeneity of appearance or other optical effects does not entail a substantial modification of the color of the mixture, which is, for example, substantially adapted to the flesh tone of the user.

Especially in exemplary embodiments in which mainly the coverage varies, the regulating member may comprise at least two successive regulating positions and the variation in color $\Delta E$ (in the CIE Lab space) of the mixture between the two successive positions of the regulating member may be less than or equal to about 0.8, for example. In exemplary embodiments, the variation in color $\Delta E$ of the mixture between two extreme positions of the regulating member may be, for example, less than or equal to about 2, for example, less than or equal to 0.8.

In exemplary embodiments, the device may be configured to deliver at least one item of information concerning the relative proportion of the first and second compositions in the mixture as a function of the setting chosen by the user, and/or at least one item of information concerning at least one optical property of the mixture as a function of the setting chosen by the user.

Modes of Distribution and Packaging

In exemplary embodiments, the device may comprise, where appropriate or desired, an applicator for applying the mixture. In exemplary embodiments, the applicator may comprise, for example, an at least partially elastically deformable structure, especially a foam, which may or may not be flocked.

Alternatively, the device may not be provided with an applicator for application of the mixture, the application then being made directly onto the area to be made up or after depositing the mixture in the palm of the hand, on a finger or in a dish, for example.

In exemplary embodiments, the device may not be provided with a pump, or, conversely, may comprise at least one pump for distributing the compositions or the mixture. In exemplary embodiments, the device may comprise, for example, two independent pumps respectively associated with the two compositions. The pump(s) may or may not be manual, with an air intake or with no air intake.

In exemplary embodiments, the mixture or at least one of the compositions may be distributed, where appropriate or desired, in the form of a spray.

In exemplary embodiments, each of the compositions may preferably be packaged in a container of the device, including a flexible or non-flexible wall.

In exemplary embodiments, at least one of the first and second compositions may be contained in a removable or non-removable container of the device. In exemplary embodiments, the containers may be solidly attached and may constitute a refill unit, the combination of the two containers possibly being removable. The containers containing the compositions may or may not be pressurized.

In exemplary embodiments, at least one composition may be contained in a flexible bag configured in a container, or may be directly contained in a container without such an intermediate bag.

The containers containing the compositions may or may not have the same capacities. For example, in exemplary embodiments, the container containing the first composition may have a capacity of greater than or equal to twice, or even three times or more than that of the container containing the second composition.

In exemplary embodiments, at least one container may or may not be at least partially transparent.

In exemplary embodiments, at least one container may contain, where appropriate or desired, a bead for homogenizing its contents.

In exemplary embodiments, the containers may be juxtaposed or may be otherwise configured, especially concentrically, or may be vertically superposed. Preferably, the device is configured to be held entirely in one hand.

Other

Exemplary embodiments of the invention may provide an assembly comprising: a device for packaging and distributing at least a first composition and a second composition different from the first composition, the two compositions being able to be mixed together for the purpose of applying them to keratin materials, the device being configured to separately store the first and second compositions, at least one of the first and second compositions containing at least one coloring agent, the device comprising a regulating member configured to allow a user to vary the relative proportion of at least one composition in the obtained mixture, and at least one of: at least one item of information relating to a visual result of application of the mixture to keratin materials, for example, associated with at least one position of the regulating member; and at least one item of information relating to a skin color, for example, a skin color to which at least one of the compositions is suited.

The term "visual result of application" denotes the appearance of the mixture after applying it to the surface that it is intended to cover, for example skin, mucous membranes or integuments. In exemplary embodiments, the information relating to the visual result of application may, for example, give information regarding the color of the mixture that may be observed after application to the surface, under normal application conditions.

In such exemplary embodiments, the relative proportion may condition the color of the mixture and/or an optical effect other than the color.

Thus, in exemplary embodiments, only the color of the mixture may vary, for example, as a function of the position of the regulating member.

In exemplary embodiments, the assembly may, for example, comprise a chart comprising at least two representations representing different appearances of the product according to the position of the regulating member, for example, different colors and/or different degrees of gloss, non-homogeneity of appearance, intensity of the variation of light as a function of the angle of observation, intensity of diffraction of light, or coverage.

In exemplary embodiments, the information, materialized by the different representations, may be given directly on the device, for example, in the form of a scale configured to correspond with an index of the regulating member, or on the packaging or supporting information, such as instructions for use, included with the device.

In exemplary embodiments, the regulating member may provide at least two positions corresponding to different relative proportions of first and second compositions in the mixture, and at least one position of the regulating member may be associated with at least one item of information representative of a visual result of application. In exemplary embodiments, one position of the regulating member may be associated, for example, with a colored mark corresponding, for example, to the color of the user's skin or to a desired color.

In exemplary embodiments, the assembly may be configured to deliver a foundation as a function of the degree of tanning of the user's skin. For example, at the start of the summer season, the mixture may be lighter than at the end of the season.

Uses

In exemplary embodiments, the assembly may thus comprise, where appropriate or desired, comments such as "more tanned complexion", "paler complexion" or "natural complexion", associated, for example, with different positions of the regulating member.

Exemplary embodiments of the invention may provide use of a device or of an assembly as defined above for making up skin, at least one of the compositions being a foundation.

Exemplary embodiments of the invention may provide use of a device or an assembly as defined above for making up lips, at least one of the compositions being a liquid lipstick.

Exemplary embodiments of the invention may provide use of a device or an assembly as defined above for making up nails, at least one of the compositions being a nail varnish.

Exemplary embodiments of the invention may provide use of a device or an assembly as defined above for making up eyelashes, at least one of the compositions being a mascara.

Makeup Processes

Exemplary embodiments of the invention may provide use of a device as defined above for coloring keratin fibers, at least one of the compositions being a coloring product.

Exemplary embodiments of the invention may provide a process for making up keratin materials, for example skin, lips or integuments, in which a mixture of the two compositions contained in the device or the assembly is applied to skin, lips or integuments.

In exemplary embodiments, at least one of the first and second compositions may be selected, for example, as a function of the color of the user's skin. Where appropriate or desired, at least one color parameter, especially the lightness and/or the hue, of the user's skin may be measured and a recommendation concerning the first composition to be used, for example, the color thereof, is issued to the user.

Exemplary embodiments of the invention may provide a process for making up keratin materials, for example, skin and/or integuments, using a device or an assembly as defined above, comprising: setting the regulating member to a first setting; making up a first area with the mixture according to the first setting; setting the regulating member to a second setting different from the first setting; and making up a second area with the mixture according to the second setting.

Exemplary embodiments of the invention may provide a process for making up keratin materials, for example skin, lips or integuments, using a device or an assembly as defined above, comprising: choosing a visual result; setting the regulating member to a setting aimed at obtaining this result; and making up an area of the skin, the lips or the integuments with the mixture according to the setting.

Ranges of Products

Exemplary embodiments of the invention may provide a range of first and second colored compositions that may be used in a device allowing them to be mixed together in a proportion selected as a function of the position of a regulating member, for example, in a device as defined above, in which the various colors of the range make it possible, alone or in combination, to obtain substantially all the skin colors of a given ethnicity, for example Caucasian, black or Asiatic.

For example, in exemplary embodiments, the range may comprise first compositions having different colors. For a first composition of the range, there is in the range a second composition which, for a given position of the regulating member, makes it possible to obtain a mixture having substantially the color of another first composition of the range. Thus, the coloration ranges obtained with the various combinations of first and second compositions may overlap.

In exemplary embodiments, the range may comprise, for example, several first compositions having tones of a first dominant, for example, yellow, with several levels of lightness, and several second compositions having tones of a second dominant, for example, red, with several levels of lightness.

In exemplary embodiments, the range may also comprise, for example, several first compositions having light tones and several second compositions having dark tones.

Exemplary embodiments of the invention may provide a plurality of first and/or second compositions, having different colors, intended for a device for mixing them together in a proportion that depends on the position of a regulating member.

Selection Process

Exemplary embodiments of the invention may provide a process for selecting the first composition of a device or assembly as defined above, comprising: measuring or evaluating at least one parameter of a user's skin color; and selecting at least one composition as a function of the parameter.

Coverage

In exemplary embodiments, in which at least one optical effect afforded by the second composition is coverage, the second composition may comprise at least one pigment and/or one filler.

In exemplary embodiments, the variation in coverage afforded by the second composition may be accompanied, where appropriate or desired, by a variation in matteness, associated, for example, with the presence of the filler.

The term "filler" denotes particles of any form, which are insoluble in the medium of the composition, irrespective of the temperature at which the composition is manufactured. A filler may be used especially to modify the rheology or the texture of the composition. The nature and amount of the particles may depend on the desired optical and mechanical properties and textures.

Examples of fillers that may be mentioned, inter alia, include talc, mica, silica, kaolin, sericite, polyamide powder, polyolefin powder, for example, polyethylene powder, polytetrafluoroethylene powder, polymethyl methacrylate powder, polyurethane powder, starch powders and silicone resin beads.

In exemplary embodiments, by varying the amount of at least one pigment and/or of filler in the mixture, by varying the relative proportion of the second composition in the mixture, a more or less covering mixture may be obtained, i.e., a mixture having a larger or smaller covering power. In exemplary embodiments, a user may thus choose to apply to his skin, lips or integuments a product that is or is not covering, for example, depending on whether or not the made-up area comprises defects.

Measurement of the Covering Power

To measure the covering power of a composition, the process may be performed in the following manner.

The composition is spread to a thickness of 30 µm onto an Erichsen type 24/5 contrast card, with a black background and a white background, and the color is measured using a calorimeter, for example, of commercial reference CR-300.

Similar spreadings are made on two other contrast cards and three measurements are taken on each card. The average corresponding to these nine measurements is then calculated.

The covering power is inversely proportional to the variation in color ($\Delta E \times 100$) between the measurements on the black background and on the white background.

In exemplary embodiments in which the variation in coverage is obtained at least partly by pigments, the first and second compositions may comprise the same pigment(s), in the same relative proportions within each composition.

This may make it possible to limit the possible variation in color during the mixing of the two compositions.

In exemplary embodiments, the variation in the covering power $1/(\Delta E \times 100)$ between two positions of the regulating member may be, for example, between 1% and 50%, better still between 1% and 30%, and even better still between 1% and 10%.

Variation of the Color as a Function of the Angle of Observation

In exemplary embodiments in which at least one optical effect afforded by the second composition is the variation in color as a function of the angle of observation, the second composition may comprise at least one goniochromatic coloring agent.

As used herein, the term "goniochromatic coloring agent" means a coloring agent for obtaining, when the composition is spread onto a support, a color trajectory in the plane a*b* of the CIE 1976 colorimetric space that corresponds to a variation Dh of the angle of hue h of at least 20° when the angle of observation is varied relative to the normal between 0° and 80°, for an angle of light incidence of 45°.

The color trajectory may be measured, for example, using an Instrument Systems brand spectrogonioreflectometer of reference GON 360 Goniometer, after the second composition has been spread in fluid form to a thickness of 300 µm using an automatic spreader onto an Erichsen brand contrast card of reference Typ 24/5, the measurement being taken on the black background of the card.

As used herein, a goniochromatic coloring agent makes it possible to observe a color change, also known as a "color flop", as a function of the angle of observation.

In exemplary embodiments, the goniochromatic coloring agent may be selected, for example, from interference multilayer structures and liquid-crystal coloring agents.

In exemplary embodiments, the multilayer structure may comprise, for example, at least two layers, each layer being made, for example, from at least one material selected from: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys and polymers, and combinations thereof.

In exemplary embodiments, the multilayer structure may or may not have, relative to a central layer, symmetry regarding the chemical nature of the stacked layers. Different effects may be obtained depending on the thickness and the nature of the various layers.

Examples of symmetrical interference multilayer structures that may be used in compositions in exemplary embodiments include, for example, the following: $Fe_2O_3/SiO_2/Fe_2O_3/SiO_2/Fe_2O_3$, a pigment including this structure being sold under the name Sicopearl by the company BASF; $MoS_2/SiO_2$/mica-oxide/$SiO_2/MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments including these structures being sold under the name Xirona by the company Merck (Darmstadt).

In exemplary embodiments, the liquid-crystal coloring agents may comprise, for example, silicones or cellulose ethers on which are grafted mesomorphic groups.

In exemplary embodiments, liquid-crystal goniochromatic particles that may be used, for example, include those sold by the company Chenix and also those sold under the name Helicone® HC by the company Wacker.

In exemplary embodiments, goniochromatic coloring agents that may also be used include certain nacres, pigments with effects on synthetic substrate, especially a substrate of alumina, silica, borosilicate, iron oxide or aluminium type, or interference holographic flakes derived from a polyterephthalate film.

In exemplary embodiments, the material may also comprise dispersed goniochromatic fibers. Such fibers may be less than 80 µm long, for example.

In exemplary embodiments, the variation in color as a function of the angle of observation may be proportionately stronger the greater the relative proportion of second composition in the mixture.

Diffraction of Light

In exemplary embodiments in which at least one optical effect afforded by the second composition is diffraction of light, the second composition may comprise at least one diffractive pigment.

As used herein, the term "diffractive pigment" denotes a pigment configured to producing a color variation according to the angle of observation when lit with white light, on account of the presence of a structure that diffracts light.

A diffractive pigment may comprise a diffracting network capable, for example, of diffracting an incident monochromatic light ray in defined directions.

The diffraction network may comprise a periodic unit, especially a line, the distance between two adjacent units being of the same order of magnitude as the wavelength of the incident light.

When the incident light is polychromatic, the diffraction network may separate the various spectral components of the light and produce a rainbow effect.

Reference may appropriately be made regarding the structure of diffractive pigments to the article "*Pigments Exhibiting Diffractive Effects*" by Alberto Argoitia and Matt Witzman, 2002, Society of Vacuum coaters, $45^{th}$ Annual Technical Conference Proceedings 2002.

In exemplary embodiments, the diffractive pigment may be made with units having different profiles, especially triangular, symmetrical or non-symmetrical, in gaps, of constant or non-constant width, or sinusoidal.

In exemplary embodiments, the spatial frequency of the network and the depth of the units may be selected as a function of the degree of separation of the various orders desired. The frequency may range, for example, between 500 and 3000 lines per mm.

In exemplary embodiments, preferably, the particles of the diffractive pigment may each have a flattened form, especially in the form of platelets.

In exemplary embodiments, the same pigment particle may comprise two crossed, perpendicular or non-perpendicular diffraction networks.

In exemplary embodiments, the diffractive pigment may have a multilayer structure comprising a layer of a reflective material, covered at least on one side with a layer of a dielectric material. The latter material may give the diffractive pigment better rigidity and durability. The dielectric material may thus be selected, for example, from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF and combinations thereof. The reflective material may be selected, for example, from metals and alloys thereof, and also from non-metallic reflective materials. Among the metals that may be used, mention may be made of Al, Ag, Cu, Au, Pt, Sn, Ti, Pd, Ni, Co, Rd, Nb and Cr, and materials, combinations or alloys thereof. Such a reflective material may, by itself, constitute the diffractive pigment, which will then be monolayer.

Alternatively, in exemplary embodiments, the diffractive pigment may comprise a multilayer structure comprising a core of a dielectric material covered with a reflective layer at least on one side, or even totally encapsulating the core. A layer of a dielectric material may also cover the reflective layer(s). The dielectric material used in such embodiments may then preferably be mineral, and may be selected, for example, from metal fluorides, metal oxides, metal sulfides, metal nitrides, and metal carbides, and combinations thereof. The dielectric material may be in crystalline, semi-crystalline or amorphous form. In this configuration, the dielectric material may be selected, for example, from the following materials: $MgF_2$, SiO, $SiO_2$, $Al_2O_3$, $TiO_2$, WO, AlN, BN, $B_4C$, WC, TiC, TiN, $N_4Si_3$, ZnS, glass particles and carbons of diamond type, and combinations thereof.

Alternatively, in exemplary embodiments, the diffractive pigment may be composed of a preformed dielectric or ceramic material such as a mineral in natural leaflet form, for example, mica perovskite or talc, synthetic leaflets formed from glass, alumina, $SiO_2$, carbon, an iron oxide/mica, mica coated with BN, BC, graphite or bismuth oxychloride, and combinations thereof.

Instead of a layer of a dielectric material, other materials that improve the mechanical properties may be suitable for use. Such materials may comprise silicone, metal suicides, semiconductive materials formed from elements of groups III, IV and V, metals with a cubic-centred crystal structure, cermet compositions or materials and semiconductive glasses, and various combinations thereof.

The diffractive pigment used may be selected especially from those described in the U.S. Patent Application Publication No. 2003/0031870, published Feb. 13, 2003.

A diffractive pigment may comprise, for example, the following structure: $MgF_2/Al/MgF_2$, a diffractive pigment including this structure being sold under the name Spectraflair 1400 Pigment Silver by the company Flex Products, or Spectraflair 1400 Pigment Silver FG. The weight proportion of $MgF_2$ may be between 80% and 95% of the total weight of the pigment.

In exemplary embodiments, the amount of diffractive pigment may vary, by weight, relative to the total weight of the second composition, for example from 0.1% to 5%, or even from 0.5% to 5%, or alternatively from 0.5% to 2.5%, for example about 1%.

In exemplary embodiments, the size of the diffractive pigment may be, for example, between 5 and 200 μm and better still between 5 and 100 μm, for example between 5 and 30 μm. The term "size" means the size given by the statistical particle size distribution to half of the population, which is referred to as the D50.

In exemplary embodiments, the thickness of the diffractive pigment particles may be less than or equal to 3 μm and better still 2 μm, for example, about 1 μm.

In exemplary embodiments, the diffractive pigment may be selected such that it is possible to observe in the second composition, for incident light at 45° and a variation of the angle of observation of between 30° and −10°, a variation Dh in the angle of hue of the second composition, in the CIE 1976 plane, of at least 50°, better still of at least 70°, or even at least 80° or 90°, or even at least 100°.

The measurement is performed while the composition is spread out using an automatic spreader to a thickness of 150 μm on the black background of a conventional contrast card, especially of Erichsen brand and of reference Typ 24/5.

A spectrogonioreflectometer with incident light at 45° and a D65 illuminant is used. The machine is in "10° observer" mode, the analysed spectrum being 400-700 nm (in 5 nm steps). The spectrogonioreflectometer used is the machine of Instrument Systems brand and of reference GON 360 Goniometer.

A negative angle of observation corresponds to an observation in the half-plane opposite that from which the light arrives, relative to the normal to the illuminated surface.

In exemplary embodiments, for an application especially to nails, the variation Dh may preferably be at least 180°, more preferably at least 270°, or even about 360° or more, for example.

In exemplary embodiments, for a gloss, the variation Dh of the angle of hue of the second composition may be at least 90°, between angles of observation of 30° and −10°.

The diffractive effect may be proportionately more visible and stronger the greater the relative proportion of second composition in the mixture. Thus, the user may select, by adjusting the regulating member of the device, to diffract more or less light.

Variation of the Homogeneity of Appearance of the Mixtures

In exemplary embodiments in which the at least one optical effect afforded by the second composition comprises inhomogeneity of appearance of the mixture, the second composition may comprise, for example, reflective or colored particles, which are visible to the naked eye, especially flakes or fibers.

Variation of the Gloss

In exemplary embodiments in which the at least one optical effect afforded by the second composition comprises gloss, the second composition may comprise, for example, reflective particles and/or nacres or alternatively an oily phase.

The mean gloss of the second composition may be greater than a certain threshold. The term "mean gloss" denotes the gloss as may be measured using a glossmeter, in a conventional manner, by the following method.

Measurement of the Mean Gloss

A layer 30 μm thick of the composition whose mean gloss it is desired to evaluate is spread onto a Leneta brand contrast card of reference Form 1A Penopac, using an automatic spreader. The layer covers at least the white background of the card. The gloss at 20° is then measured on the white background using a Byk Gardner brand glossmeter of reference microTri-Gloss.

In exemplary embodiments, the mean gloss values of the mixture may be between 0.01 and 60 for example, better still between 0.5 and 40 and even better still between 1 and 20.

Reflective Particles

As used herein, the term "reflective particles" denotes particles whose size, structure, especially the thickness of the layer(s) of which they are made and of their physical and chemical nature, and the surface state, allow them to reflect incident light. The reflection may, where appropriate or desired, have an intensity sufficient to create at the surface of the composition or of the mixture, when it is applied to the support to be made up, points of overbrightness that are visible to the naked eye, i.e. more luminous points that contrast with their environment by appearing to sparkle.

In exemplary embodiments, the reflective particles may be selected so as not to significantly alter the coloration effect generated by the coloring agents with which they are combined, and more particularly so as to optimize this effect in terms of color yield. They may more particularly have a yellow, pink, red, bronze, orange, brown, gold and/or coppery color or glint.

In exemplary embodiments, the reflective particles may be present in the second composition in a content ranging from 0.5% to 60%, especially from 1% to 30% by weight, in particular from 2% to 20% by weight or even from 3% to 10% by weight relative to the total weight of the second composition.

In exemplary embodiments, the particles may have varied forms and may especially be in platelet or globular form, in particular spherical.

Irrespective of their form, the reflective particles may or may not have a multilayer structure, and, in the case of a multilayer structure, for example at least one layer of uniform thickness, especially a reflective material.

In exemplary embodiments in which the reflective particles do not have a multilayer structure, they may be composed, for example, of metal oxides, especially titanium or iron oxides obtained via synthesis.

In exemplary embodiments in which the reflective particles have a multilayer structure, they may comprise, for example, a natural or synthetic substrate, especially a synthetic substrate at least partially coated with at least one layer of a reflective material, especially of at least one metal or metallic material. The substrate may be a monomaterial, multimaterial, organic and/or mineral substrate.

More particularly, the substrate may be selected from glasses, ceramics, graphite, metal oxides, aluminas, silicas, silicates, especially aluminosilicates and borosilicates, and synthetic mica, and mixtures thereof, this list not being limiting.

In exemplary embodiments, the reflective material may comprise a layer of metal or of a metallic material.

Glass particles covered with a metallic layer are described especially in documents JP-A-09188830, JP-A-10158450, JP-A-10158541, JP-A-07258460 and JP-A-05017710.

As an example of reflective particles comprising a mineral substrate coated with a layer of metal, mention may also be made of particles comprising a silver-coated borosilicate substrate, also known as "white nacres".

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Irrespective of their form, the reflective particles may also be selected from particles with a synthetic substrate coated at least partially with at least one layer of at least one metallic material, especially a metal oxide, chosen, for example, from titanium oxide, especially $TiO_2$, iron oxide, especially $Fe_2O_3$, tin oxide, chromium oxide, barium sulfate and the following materials: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$ and $MoS_2$, and mixtures or alloys thereof.

As examples of such particles, mention may be made, for example, of particles comprising a synthetic mica substrate coated with titanium dioxide, or glass particles coated with either brown iron oxide, titanium oxide, tin oxide or a mixture thereof, for instance, those sold under the brand name Reflecks® by the company Engelhard.

In exemplary embodiments, the reflective particles may or may not be goniochromatic and/or may or may not be interference particles.

In exemplary embodiments, the second composition may comprise at least one nacre.

Nacres

The term "nacre" should be understood as meaning colored particles of any form, which may or may not be iridescent, especially produced by certain molluscs in their shell, or alternatively synthesized, and which have a color effect via optical interference.

The nacres may be selected from nacreous pigments such as titanium mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery color or glint.

As illustrations of nacres that may be used in exemplary embodiments, mention may be made especially of the gold-colored nacres sold especially by the company Engelhard under the name Brillant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Oils

Especially when the compositions are intended to be applied to lips, the second composition may comprise an oily phase that gives gloss, in particular, an oily phase with a refractive index of between 1.36 and 1.56, better still between 1.36 and 1.50, or even better still 1.37 to 1.49. The refractive index is measured at room temperature (25° C.) using a refractometer.

An oily phase as described in patent application EP-A-792 637, the content of which is incorporated herein by reference in its entirety, may be selected.

In exemplary embodiments, the second composition may contain, for example, at least one carbon-based oil, hydrocarbon-based oil, fluoro oil and/or silicone oil, of mineral, plant or synthetic origin.

The term "hydrocarbon-based oil" means oils mainly containing carbon atoms and hydrogen atoms and, in particular, alkyl or alkenyl chains, for instance, alkanes or alkenes, but also oils with an alkyl or alkenyl chain comprising one or more alcohol, ether, ester and/or carboxylic acid groups.

As oils that may be used, mention may thus be made, this list not being limiting, of hydrocarbon-based oils of mineral or synthetic origin such as linear or branched hydrocarbons, for instance liquid paraffin or its derivatives, liquid petroleum jelly, polydecenes, hydrogenated polyisobutene such as Parleam® sold by the company Nippon Oil Fats, squalane of synthetic or plant origin; oils of animal origin, such as mink oil, turtle oil or perhydrosqualene; hydrocarbon-based oils of plant origin with a high triglyceride content consisting of fatty acid esters of glycerol, the fatty acids of which may have varied chain lengths, the said chains possibly being linear or branched, and saturated or unsaturated, for instance sweet almond oil, beauty-leaf oil, palm oil, grapeseed oil, sesame oil, arara oil, rapeseed oil, sunflower oil, cottonseed oil, apricot oil, castor oil, alfalfa oil, marrow oil, blackcurrant oil, macadamia oil, musk rose oil, hazelnut oil, avocado oil, jojoba oil, olive oil or cereal germ oil (from corn, wheat, barley or rye); fatty acid esters and especially esters of lanolic acid, of oleic acid, of lauric acid or of stearic acid; synthetic esters such as, for example, purcellin oil (cetostearyl octanoate), isononyl isononanoate, $C_{12}$ to $C_{15}$ alkyl benzoate, 2-ethylhexyl palmitate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyldodecyl myristate, 2-diethylhexyl succinate, diisostearyl malate, or glyceryl or diglyceryl triisostearate; hydroxylated esters, for instance isostearyl lactate; pentaerythritol esters; $C_8$-$C_{26}$ higher fatty acids such as oleic acid, linoleic acid, linolenic acid or isostearic acid; $C_8$-$C_{26}$ higher fatty alcohols such as oleyl alcohol, linoleyl alcohol, linolenyl alcohol, isostearyl alcohol or octyldodecanol; synthetic esters containing at least 7 carbon atoms, silicone oils such as polydimethylsiloxanes (PDMSs) that are liquid at room temperature, linear, and optionally phenylated, such as phenyltrimethicones, phenyltrimethylsiloxydiphenylsiloxanes, diphenyldimethicones, diphenylmethyldiphenyltrisiloxanes, liquid 2-phenylethyl trimethylsiloxysilicates, optionally substituted with aliphatic and/or aromatic groups, for instance alkyl, alkoxy or phenyl groups that are pendent and/or at the end of a silicone chain, these groups containing from 2 to 24 carbon atoms and being optionally fluorinated, or with functional groups such as hydroxyl, thiol and/or amine groups; polysiloxanes modified with fatty acids, with fatty alcohols or with polyoxyalkylenes, for instance dimethicone copolyols or alkylmethicone copolyols; liquid fluorosilicones; or alternatively caprylic/capric acid triglycerides, for instance those sold by the company Stearineries Dubois or those sold under the names Miglyol 810, 812 and 818 by the company Dynamit Nobel; and mixtures thereof.

Good dispersing of the pigments and/or fillers in the second composition may also make it possible to improve the gloss of the mixture applied to the area to be made up.

In the case of a nail varnish, the gloss may be obtained by introducing into the varnish composition compounds of polyurethane and latex type, for example.

The gloss may be proportionately stronger the higher the proportion of the second composition in the mixture.

In exemplary embodiments, by adjusting the regulating member, the user may vary the relative proportions of the first and second compositions to obtain a more or less glossy or more or less matt or satin mixture.

Coloring Agents

In exemplary embodiments, at least one of the first and second compositions may comprise at least one coloring agent. The first composition and the second composition may each comprise at least one coloring agent, which may be the same coloring agent in identical or different concentrations.

The second composition may comprise a coloring agent, for example, to obtain, when mixed with the first composition, a variation in the color and/or the coverage and/or another visible optical effect.

The coloring agent may be selected, for example, from mineral pigments, organic pigments or lakes, nacreous pigments, composite pigments and liposoluble or water-soluble dyes.

The mineral pigments may be white or colored, and coated or uncoated. Mention may be made of titanium dioxide, optionally surface-treated, zirconium oxide or cerium oxide, and also iron oxide or chromium oxide, manganese violet, ultramarine blue, chromium hydrate and ferric blue. In exemplary embodiments, the pigments may represent from 0 to 40%, preferably from 1% to 35% and better still from 2% to 25% of the total weight of the composition.

The nacreous pigments may be selected from white nacreous pigments such as mica coated with titanium or with bismuth oxychloride, colored nacreous pigments such as titanium mica with iron oxides, titanium mica especially with ferric blue or with chromium oxide, titanium mica with an organic pigment of the abovementioned type, and also nacreous pigments based on bismuth oxychloride. In exemplary embodiments, they may represent from 0 to 20% and better still from 0.1% to 15% of the total weight of the composition.

The liposoluble dyes may be, for example, plant extracts, Sudan red, DC Red 17, DC Green 6, β-carotene, soybean oil, Sudan brown, DC Yellow 11, DC Violet 2, DC Orange 5 and quinoline yellow.

The water-soluble dyes may be selected, for example, from plant extracts, especially beetroot juice and methylene blue.

In exemplary embodiments, the dyes may represent, for example, from 0.1% to 20% or even from 0.1% to 6% of the weight of the first or second composition.

The coloring agent may comprise at least one organic dyestuff, for example, at least one organic pigment and/or at least one organic lake.

The organic dyestuff may be selected, for example, from particulate materials that are insoluble in the physiologically acceptable medium of the composition.

The organic dyestuff may comprise, for example, organic pigments or lakes, which may be selected from the following materials, and mixtures thereof:
  cochineal carmine,
  organic pigments of azo, anthraquinone, indigoid, xanthene, pyrene, quinoline, triphenylmethane or fluorane dyes,
  organic lakes or insoluble sodium, potassium, calcium, barium, aluminium, zirconium, strontium or titanium salts of acidic dyes such as azo, anthraquinone, indigoid, xanthene, pyrene, quinoline, triphenylmethane or fluorane dyes, these dyes possibly comprising at least one carboxylic or sulfonic acid group.

Among the organic pigments that may especially be mentioned are those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The organic dyestuff may comprise an organic lake supported on an organic support such as colophony or aluminium benzoate, for example.

Among the organic lakes that may be mentioned in particular are those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake, FD&C Yellow No. 6 Aluminium lake.

The chemical materials corresponding to each of the organic dyestuffs mentioned above are mentioned in the publication "International Cosmetic Ingredient Dictionary and Handbook", 1997 edition, pages 371 to 386 and 524 to 528, published by "The Cosmetic, Toiletry, and Fragrance Association", the content of which is incorporated herein by reference in its entirety.

The coloring agent may comprise a composite pigment.

Composite Pigments

The composite pigment may be composed especially of particles comprising:

a mineral core and at least one at least partial coating of at least one organic dyestuff.

At least one binder may advantageously contribute to the attaching of the organic dyestuff to the mineral core.

The composite pigment particles may have varied forms. The particles may especially be in platelet or globular form, in particular spherical, and may be hollow or solid. The term "platelet form" denotes particles for which the ratio of the largest size to the thickness is greater than or equal to 5.

In exemplary embodiments, a composite pigment may have, for example, a specific surface area of between 1 and 1000 $m^2/g$, especially between 10 and 600 $m^2/g$ approximately and in particular between 20 and 400 $m^2/g$ approximately. The specific surface area is the value measured by the BET method.

The first and/or second composition may comprise one or more composite pigments as defined above.

The mineral core of the composite pigment may be of any form that is suitable for fixing particles of organic dyestuff, for example, spherical, globular, granular, polyhedral, acicular, fusiform, flattened in the form of a flake, a rice grain or a scale, and also a combination of these forms, this list not being limiting.

In exemplary embodiments, the ratio of the largest size of the core to its smallest size may be between 1 and 50.

In exemplary embodiments, the mineral core may have a size of between about 1 nm and about 100 nm, or even between about 5 nm and about 75 nm, for example, between about 10 nm and about 50 nm.

The mineral core may be made of a material selected from the non-limiting list comprising metal salts and metal oxides, especially titanium oxide, zirconium oxide, cerium oxide, zinc oxide, iron oxide, ferric blue, aluminium oxide and chromium oxide, aluminas, glasses, ceramics, graphite, silicas, silicates, especially aluminosilicates and borosilicates, and synthetic mica, and mixtures thereof.

Titanium oxide, especially $TiO_2$, iron oxide, especially $Fe_2O_3$, cerium oxide, zinc oxide and aluminium oxide, and silicates, especially aluminosilicates and borosilicates, are most particularly suitable.

The mineral core may be colored, where appropriate or desired.

The organic dyestuff may be as defined above.

The binder of the composite pigment may be of any type provided that it allows the organic dyestuff to adhere to the surface of the mineral core.

The binder may be selected especially from a non-limiting list comprising silicone materials, polymeric or oligomeric materials or the like, and in particular from organosilanes, fluoroalkyl organosilanes and polysiloxanes, for example polymethylhydrogenosiloxane, and also various coupling agents, such as coupling agents based on silanes, titanates, aluminates and zirconates, and mixtures thereof.

Other Ingredients

In exemplary embodiments, at least one of the first and second compositions may comprise ingredients other than those described above, especially at least one solvent, a fatty phase, a film-forming polymer and/or a dermatological or cosmetic active agent, especially as a function of the galenical form.

Solvents

The first and/or second composition may comprise at least one aqueous or organic solvent.

In exemplary embodiments in which the first and/or the second composition comprises one or more organic solvents, the solvents may be present in a content ranging from 0.1% to 99% by weight relative to the total weight of the composition concerned.

In general, the amount of solvent(s), especially organic solvent(s), will depend on the nature of the support onto which the composition is intended to be applied.

The first and/or second composition may comprise at least one organic solvent selected from the following:
- ketones that are liquid at room temperature, such as methyl ethyl ketone, methyl isobutyl ketone, diisobutyl ketone, isophorone, cyclohexanone and acetone;
- alcohols that are liquid at room temperature, such as ethanol, isopropanol, diacetone alcohol, 2-butoxyethanol or cyclohexanol;
- glycols that are liquid at room temperature, such as ethylene glycol, propylene glycol, pentylene glycol or glycerol;
- propylene glycol ethers that are liquid at room temperature, such as propylene glycol monomethyl ether, propylene glycol monomethyl ether acetate and dipropylene glycol mono-n-butyl ether;
- short-chain esters (containing from 3 to 8 carbon atoms in total), such as ethyl acetate, methyl acetate, propyl acetate, n-butyl acetate or isopentyl acetate; and
- alkanes that are liquid at room temperature, such as decane, heptane, dodecane or cyclohexane.

The first and/or second composition may also comprise water or a mixture of water and of hydrophilic organic solvents commonly used in cosmetics, for instance alcohols and especially linear or branched lower monoalcohols containing from 2 to 5 carbon atoms, for instance, ethanol, isopropanol and n-propanol, polyols, for instance glycerol, diglycerol, propylene glycol, sorbitol, penthylene glycol and polyethylene glycols. The first and/or second composition may also contain hydrophilic $C_2$ ethers and $C_2$-$C_4$ aldehydes. Water or a mixture of water and of hydrophilic organic solvents may be present in the first and/or second composition in a content ranging, for example, from 0% to 90%, especially from 0.1% to 90% by weight, preferably from 0% to 60% by weight and especially from 0.1% to 60% by weight, relative to the total weight of the composition.

Fatty Phase

The first and/or second composition, for example, when intended to be applied to lips, may comprise a fatty phase and especially at least one fatty substance that is liquid at room temperature (25° C.) and/or a fatty substance that is solid at room temperature, such as waxes, pasty fatty substances and gums, and mixtures thereof. The fatty phase may also contain lipophilic organic solvents.

The first and/or second composition may contain, for example, a continuous fatty phase, which may contain less than 5% water and especially less than 1% water relative to its total weight, and in particular may be in anhydrous form.

As fatty substances that are liquid at room temperature, often referred to as "oils", mention may be made of: hydrocarbon-based plant oils such as liquid triglycerides of fatty acids of 4 to 10 carbon atoms, for instance heptanoic or octanoic acid triglycerides, or alternatively sunflower oil, corn oil, soybean oil, grapeseed oil, sesame oil, apricot oil, macadamia oil, castor oil, avocado oil, caprylic/capric acid triglycerides, jojoba oil, shea butter oil, lanolin oil and acetylated lanolin oil; linear or branched hydrocarbons of mineral or synthetic origin, such as liquid paraffins and derivatives thereof, petroleum jelly, polydecenes and hydrogenated polyisobutene such as parleam; synthetic esters and ethers, especially of fatty acids, for instance purcellin oil, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and heptanoates, octanoates or decanoates of fatty alcohols; isononyl isonanoate, isopropyl lanolate, tridecyl trimellilate or diisostearyl malate; polyol esters, for instance propylene glycol dioctanoate, neopentyl glycol diheptanoate or diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol or oleyl alcohol; partially hydrocarbon-based and/or silicone-based fluoro oils; silicone oils, for instance volatile or non-volatile, linear or cyclic polydimethylsiloxanes (PDMS) that are liquid or pasty at room temperature, for instance cyclomethicones or dimethicones, optionally comprising a phenyl group, for instance phenyl trimethicones, phenyltrimethylsiloxydiphenylsiloxanes, diphenylmethyldimethyltrisiloxanes, diphenyl dimethicones, phenyl dimethicones and polymethylphenylsiloxanes; mixtures thereof. The oils may be present in a content ranging from 0.01% to 90% and better still from 0.1% to 85% by weight relative to the total weight of the composition.

At least one of the compositions may comprise a pasty fatty substance, a wax or a gum.

The pasty fatty substances may generally be hydrocarbon-based compounds with a melting point of between 25 and 60° C. and preferably between 30 and 45° C., and/or a hardness of between 0.001 and 0.5 MPa and preferably between 0.005 and 0.4 MPa, for instance, lanolins and derivatives thereof.

The waxes may be solid at room temperature (25° C.), with a reversible solid/liquid change of state, having a melting point of greater than 30° C. that may be up to 200° C., a hardness of greater than 0.5 MPa, and having in the solid state an anisotropic crystal organization. In particular, the waxes may have a melting point of greater than 25° C. and better still greater than 45° C. The waxes may be hydrocarbon-based waxes, fluoro waxes and/or silicone waxes and may be of plant, mineral, animal and/or synthetic origin. As waxes that may be used, mention may be made of beeswax, carnauba wax or candelilla wax, paraffin, microcrystalline waxes, ceresin or ozokerite; synthetic waxes, for instance polyethylene waxes or Fischer-Tropsch waxes, and silicone waxes, for instance, alkyl or alkoxy dimethicones containing from 16 to 45 carbon atoms. The composition may contain from 0 to 50% by weight or even from 1% to 30% by weight of waxes relative to the total weight of the composition.

The gums that may be used are generally high molecular weight polydimethylsiloxanes (PDMS) or cellulose gums or polysaccharides.

Film-Forming Polymer

The composition may also comprise, for example, a film-forming polymer, especially in the case of a mascara, a nail varnish or a foundation. The term "film-forming polymer" denotes a polymer configured to forming, by itself or in the presence of an auxiliary film-forming agent, a continuous film that adheres to a support, and especially to keratin materials.

Among the film-forming polymers that may be used in exemplary embodiments, mention may be made, inter alia, of synthetic polymers, of free-radical type or of polycondensate type, polymers of natural origin, such as nitrocellulose or cellulose esters, and mixtures thereof.

The film-forming polymers of free-radical type may especially be vinyl polymers or copolymers, especially acrylic polymers.

The vinyl film-forming polymers may result from the polymerization of ethylenically unsaturated monomers containing at least one acid group and/or esters of the acid monomers and/or amides of the acid monomers, for instance, α,β-ethylenically unsaturated carboxylic acids such as acrylic acid, methacrylic acid, crotonic acid, maleic acid or itaconic acid.

The vinyl film-forming polymers may also result from the homopolymerization or copolymerization of monomers selected from vinyl esters, for instance, vinyl acetate, vinyl neodecanoate, vinyl pivalate, vinyl benzoate and vinyl t-butylbenzoate, and styrene monomers, for instance, styrene and α-methylstyrene, and ethylenic, propylenic or butylenic monomers.

Among the film-forming polycondensates that may be mentioned are polyurethanes, polyesters, polyesteramides, polyamides and polyureas, this list not being limiting.

The optionally modified polymers of natural origin may be selected from shellac resin, sandarac gum, dammar resins, elemis gums, copal resins, cellulose-based polymers, such as nitrocellulose, ethylcellulose or nitrocellulose esters chosen, for example, from cellulose acetate, cellulose acetobutyrate and cellulose acetopropionate, and mixtures thereof.

The film-forming polymer may be present in the form of solid particles in aqueous or oily dispersion, which are generally known as latices or pseudolatices. The film-forming polymer may comprise one or more stable dispersions of generally spherical polymer particles of one or more polymers, in a physiologically acceptable liquid fatty phase. The dispersions are generally known as NADs (non-aqueous dispersions) of polymer, as opposed to latices, which are aqueous polymer dispersions. The dispersions may especially be in the form of polymer nanoparticles as a stable dispersion in the said fatty phase. The nanoparticles are preferably between 5 and 600 nm in size. The techniques for preparing these dispersions are well known.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasei Kogyo; or alternatively the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ by the company Eastman Chemical Products.

In exemplary embodiments, the first and/or second composition may also comprise an auxiliary film-forming agent that promotes the formation of a film with the film-forming polymer.

In exemplary embodiments, the first and/or second composition may comprise at least one cosmetic or dermatological active agent. As cosmetic, dermatological, hygiene or pharmaceutical active agents that may be used in exemplary embodiments, mention may be made of moisturizers (polyols, for instance glycerol), vitamins (C, A, E, F, B or PP), essential fatty acids, essential oils, ceramides, sphingolipids, liposoluble sunscreens or sunscreens in the form of nanoparticles, specific skin treating active agents (protective agents, antibacterial agents, antiwrinkle agents, etc.), and self-tanning agents. The active agents may be used, for example, in concentrations of from 0 to 20% and especially from 0.001% to 15% relative to the total weight of the composition.

In exemplary embodiments, the first and/or second composition may also contain ingredients commonly used in cosmetics, for instance, thickeners, surfactants, trace elements, moisturizers, softeners, sequestrants, fragrances, acidifying or basifying agents, preserving agents, antioxidants, UV-screening agents and dyes, or mixtures thereof.

In exemplary embodiments, the first and/or second composition may comprise, depending on the envisaged type of application, the constituents conventionally used in the fields under consideration, which are present in an amount appropriate to the desired galenical form.

Galenical Forms

The first and/or second composition may be in various forms, depending on its intended use. Each composition may thus be in any galenical form normally used for topical application, and especially in anhydrous form, in the form of an oily or aqueous solution, an oily or aqueous gel, an oil-in-water, water-in-oil, wax-in-water or water-in-wax emulsion, a multiple emulsion, or a dispersion of oil in water by vesicles located at the oil/water interface.

In exemplary embodiments, one of the compositions, especially the second composition, may be in the form of a powder.

Each composition may also be in various other forms, for example a gel.

In exemplary embodiments, the mixture obtained may constitute a makeup composition, for example, a lipstick, a liquid gloss, a makeup rouge, a fluid foundation, a concealer product, an eye contour product, an eyeliner, a mascara, a nail varnish, a fluid eyeshadow, a body makeup product, a hair makeup product or alternatively a skin coloring product.

BRIEF DESCRIPTION OF THE DRAWINGS

Various exemplary details of devices that are suitable for packaging and distributing the first and second compositions are described with reference to the drawings, in which:

FIG. 1 is an elevated, schematic view of an exemplary device;

FIG. 2 is an elevated, schematic partial view of another exemplary device;

FIGS. 3 and 4 show, in axial, schematic and partial cross sectional views, an exemplary device comprising an applicator;

DETAILED DESCRIPTION OF EMBODIMENTS

Figure 5:
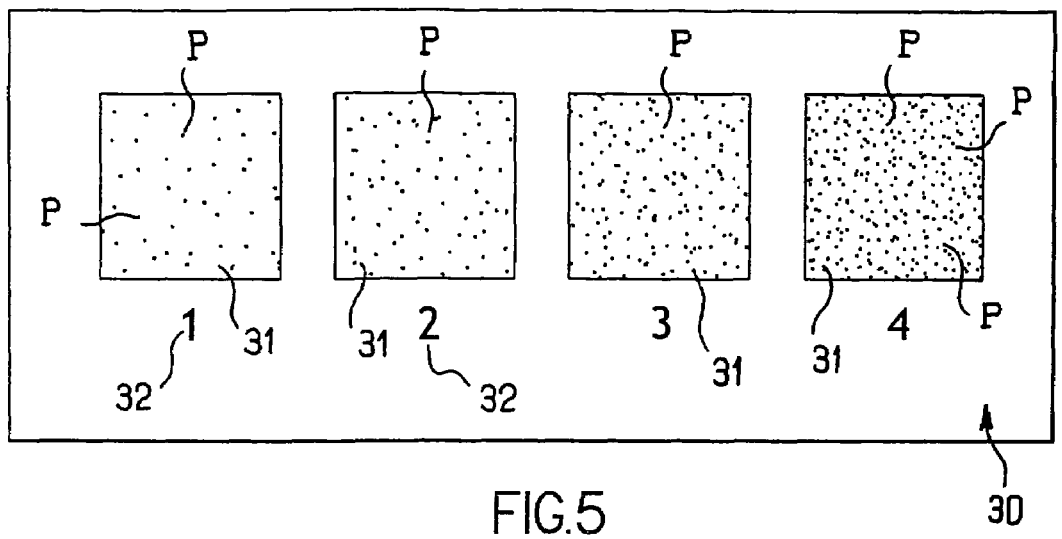
FIG. 5 shows schematically a chart that may be combined with the device.

The exemplary device 1 shown in FIG. 1 comprises two containers 2 and 3 respectively containing first $C_1$ and second $C_2$ compositions intended to be mixed together.

The device 1 comprises a distributing head 4 comprising, in the exemplary embodiment, a fixed base part 5 and a push-button 6 that is mobile relative to the base part and configured to actuate one or two pumps, not shown in the figures. The push-button 6 is provided, in the exemplary embodiment shown, with a single distribution orifice 7 to distribute the mixture of compositions $C_1$ and $C_2$.

The orifice 7 may or may not be fitted with a flap valve so as to protect the compositions from intrusion of any external component.

The base part 5 may comprise at least one window 9, or two diametrically opposite windows, only one of which is visible in FIG. 1, giving access to a regulating member 10 for regulating the proportions of compositions $C_1$ and $C_2$ in the distributed mixture.

The regulating member 10 is, in the exemplary embodiment, rotary around the longitudinal axis X of the device 1 and comprises a series of positions 11, for example marked by figures, enabling the user, by positioning one of them under a reference mark 12 of the base part 5, to select a mixture to be distributed.

In the exemplary embodiment shown in FIG. 1, the mixing of compositions $C_1$ and $C_2$ in proportions determined by the setting of the regulating member 10 is performed inside the device 1, but it is also contemplated for the mixing to be performed after leaving the device 1, for example, with the device being equipped with two distribution orifices 7a and 7b to distribute, respectively, compositions $C_1$ and $C_2$ separately, as illustrated in FIG. 2.

As shown in FIGS. 3 and 4, the device 1 may be equipped with an applicator 20 configured to receive the mixture and to allow the user to apply the mixture. The applicators 20 shown in FIGS. 3 and 4 consist of elastically deformable components, especially porous foams.

It is contemplated that the applicator may comprise or consist of any other component, for example, a coarse brush, a comb, a fine brush, a flocked tip, a sinter, a wipe, a product block or an applicator retaining the product by capillary action.

In the exemplary embodiment in FIG. 3, the applicator is attached to a lid 21 of the device and collects the distributed mixture in the direction of the arrows onto at least a part of its outer surface 22.

In FIG. 4, the applicator 20 is attached to the device 1 so as to collect the distributed mixture in the direction of the arrows onto its inner surface 23, the product then being conveyed, for example, by pressure or capillary action, to the outer surface 22 of the applicator for application.

It is contemplated that the applicator may be attached differently to the device 1, or may have another use.

In particular, the applicator may serve to mix the two compositions, or to measure the compositions out. The applicator may be a single-use or multiple-use applicator.

One of the containers 2 and 3, or both of the containers, may be removable, so as to be able to refill the device or to personalize it as a function, for example, of the skin or the wishes of a user.

At least one of the first and second compositions may thus be selected, for example, from a range of products as a function, for example, of the user's skin color.

It is contemplated that the regulating member 10 to be non-rotary.

Other devices may be used, especially those described in European patent application EP 1 040 773 and U.S. Pat. Nos. 5,568,883, 5,971,210, 4,893,729, and 5,143,261, which are incorporated herein by reference in their entirety.

The user may benefit, where appropriate or desired, from at least one item of information representative of a visual result of the mixture, especially for a predetermined relative proportion of the first and second compositions $C_1$ and $C_2$ and/or from at least one item of information relating to a skin color to which at least one of the compositions is suited.

In exemplary embodiments, the device may comprise, for example, a chart 30 showing several of the characteristics of the mixture, for example, in the form of representations 31, of which there are four in FIG. 5.

The representations 31 are, for example, representative of visual results that may be obtained as a function of the relative proportion of the second composition in the mixture obtained.

With each representation 31 may be associated information 32 corresponding to a given positioning or setting of the regulating member.

In the exemplary embodiment, the second composition $C_2$ comprises a material for varying the homogeneity of the appearance of the mixture. The material, in this example, comprises particles P, for example, flakes that may or may not be visible to the naked eye. The larger the proportion of second composition, the greater the concentration of particles P, and the more the appearance of the mixture is flaked and non-homogeneous. If the user selects the setting "1", he will obtain a mixture whose appearance will be similar to the representation 31 associated with the FIG. "1", i.e., slightly flaked. If the user selects a setting "4", he will obtain a more flaked effect, as illustrated in the representation 31 associated with the FIG. "4".

In an exemplary embodiment not illustrated, the chart may comprise at least one colored representation representative of a skin color to which at least one of the compositions is suited, for example, to guide the user in his choice within a range of devices or of compositions according to his skin color.

Figure 6:
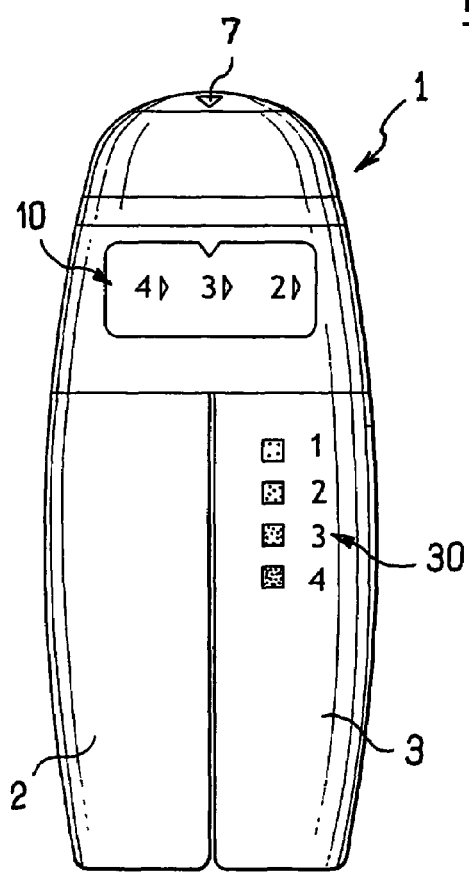
FIG. 6 is a view similar to FIG. 1 of another exemplary device.

The representations 31 or other marks or representations may be given on a notice accompanying the device 1 or alternatively may be present directly on the device itself, for example, on one of the containers, as illustrated in FIG. 6.

Figure 7:
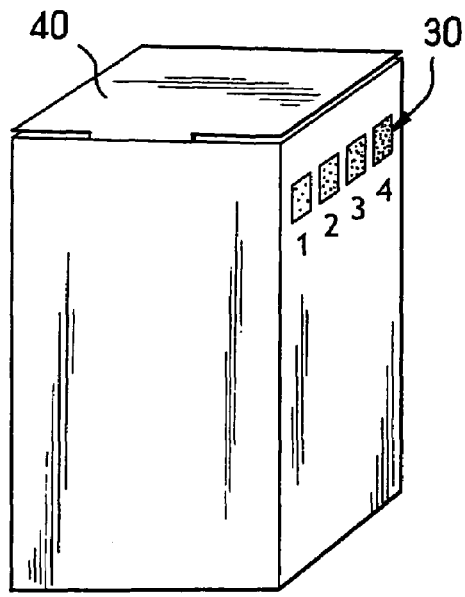
FIG. 7 shows an exemplary packaging.

The representations 31 may also be present on a packaging 40 of the device 1, as illustrated in FIG. 7, or on the regulating member itself, in place of the inscriptions 11.

Needless to say, the chart 30 may be accompanied by information relating to each position of the regulating member or to each visual result, for example, explanations regarding the optical effect obtained according to the chosen setting and/or advice regarding the use of a particular mixture, or alternatively information regarding the relative proportion of each composition in the mixture for a given position of the regulating member. Position "1" may correspond, for example, to a mixture containing 90% by weight of first composition and 10% of second composition, and position "4" to a mixture containing 30% by weight of first composition and 70% by weight of second composition.

It is contemplated that the number of positions of the regulating member may be greater or less than four, the passage from one position to another possibly being performed, where appropriate or desired, continuously, thus allowing intermediate positions corresponding to other results. The possible positions of the regulating member may also be permitted by notches.

In an exemplary embodiment not illustrated, the second composition is configured to varying the color of the mixture, as a function of its proportion in the mixture.

The device may thus comprise a color scale cooperating with an index of the regulating member, each color of the scale corresponding to the color of the mixture for a predetermined relative proportion of the compositions of the mixture.

EXAMPLES

The examples below are presented as non-limiting illustrations of exemplary embodiments.

Compositions $C_1$ and $C_2$ may be obtained according to preparation processes conventionally used in cosmetics.

| | Foundations | |
|---|---|---|
| | $C_1$ | $C_2$ |
| Example 1 | Neutral base[1] | Covering composition[3] |
| Example 2 | Neutral base[1] | Nacreous composition[4] |
| Example 3 | Neutral base[1] | Goniochromatic composition[5] |
| Example 4 | Neutral base[1] | Colored composition[6] |
| Example 5 | Colored base[2] | Covering composition[3] |
| Example 6 | Colored base[2] | Nacreous composition[4] |
| Example 7 | Colored base[2] | Goniochromatic composition[5] |
| Example 8 | Colored base[2] | Colored composition[6] |
| Example 9 | Colored base[2] | Covering colored composition[7] |

The amounts are expressed on a mass basis in all the examples.

1. The neutral base may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Water | qs 100 |

2. The colored base may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Yellow iron oxide coated with perfluoroalkyl phosphate as a dispersion in decamethylcyclopentasiloxane/dimethicone copolyol (sold under the name FA50DYF by Kobo) | 1.67 |
| Brown iron oxide coated with perfluoroalkyl phosphate as a dispersion in cyclomethicone/dimethylpolysiloxane copolyol (sold under the name FA50DRF by Kobo) | 0.45 |
| Black iron oxide coated with perfluoroalkyl phosphate as a dispersion in decamethylcyclopentasiloxane/dimethicone copolyol (sold under the name FA65DBF by Kobo) | 0.23 |
| Alumina-treated titanium oxide coated with perfluoroalkyl phosphate in decamethylcyclopentasiloxane/dimethicone copolyol (sold under the name FA65DF by Kobo) | 5.52 |
| Water | qs 100 |

3. The covering composition may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Yellow iron oxide coated with perfluoroalkyl phosphate as a dispersion in decamethylcyclopentasiloxane/dimethicone copolyol (sold under the name FA50DYF by Kobo) | 3.18 |
| Brown iron oxide coated with perfluoroalkyl phosphate as a dispersion in cyclomethicone/dimethylpolysiloxane copolyol (sold under the name FA50DRF by Kobo) | 0.86 |
| Black iron oxide coated with perfluoroalkyl phosphate as a dispersion in decamethylcyclopentasiloxane/dimethicone copolyol (sold under the name FA65DBF by Kobo) | 0.44 |
| Alumina-treated titanium oxide coated with perfluoroalkyl phosphate in decamethylcyclopentasiloxane/dimethicone copolyol (sold under the name FA65DF by Kobo) | 10.52 |
| Water | qs 100 |

4. The nacreous composition may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Nacre | 8 |
| Water | qs 100 |

Such a composition may impart gloss.

5. The goniochromatic composition may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |

| | |
|---|---|
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Interference pigment | 8 |
| Water | qs 100 |

6. The colored composition may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.6 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Yellow iron oxide coated with perfluoroalkyl phosphate as a dispersion in decamethylcyclopentasiloxane/dimethicone copolyol (sold under the name FA50DYF by Kobo) | 2.7 |
| Brown iron oxide coated with perfluoroalkyl phosphate as a dispersion in cyclomethicone/dimethylpolysiloxane copolyol (sold under the name FA50DRF by Kobo) | 1.1 |
| Black iron oxide coated with perfluoroalkyl phosphate as a dispersion in decamethylcyclopentasiloxane/dimethicone copolyol (sold under the name FA65DBF by Kobo) | 1.4 |
| Alumina-treated titanium oxide coated with perfluoroalkyl phosphate in decamethylcyclopentasiloxane/dimethicone copolyol (sold under the name FA65DF by Kobo) | 2.32 |
| Water | qs 100 |

7. The covering colored composition may have, for example, the following formulation:

| | |
|---|---|
| 1,3-Butylene glycol | 10 |
| Hectorite modified with distearyldimethylammonium chloride (sold under the name Bentone 38 V by Elementis) | 1.6 |
| Preserving agents | 0.9 |
| Cyclopentadimethylsiloxane | 15.0 |
| Isostearyl neopentanoate | 0.5 |
| Sodium chloride | 0.7 |
| Isododecane | 12.7 |
| Cyclohexadimethylsiloxane | 7.7 |
| Polydimethylsiloxane (DC 200 Fluid 5 cst sold by Dow Corning) | 2 |
| Cetyldimethicone copolyol (sold under the name Abil EM 90 by Goldschmidt) | 0.8 |
| Polyglyceryl isostearate | 0.6 |
| Isoeicosane | 2 |
| Hexyl laurate | 0.6 |
| Hollow polymethyl methacrylate microspheres (sold under the name Covabead LH85 by Wackherr) | 2 |
| Polymethyl methacrylate powder (sold under the name Jurymer MB1 by Nihon Junyaku) | 2 |
| Oxyethylenated polydimethylsiloxane (sold under the name KF-6017 by Shin-Etsu) | 5 |
| Yellow iron oxide coated with perfluoroalkyl phosphate as a dispersion in decamethylcyclopentasiloxane/dimethicone copolyol (sold under the name FA50DYF by Kobo) | 3 |
| Brown iron oxide coated with perfluoroalkyl phosphate as a dispersion in cyclomethicone/dimethylpolysiloxane copolyol (sold under the name FA50DRF by Kobo) | 1.2 |
| Black iron oxide coated with perfluoroalkyl phosphate as a dispersion in decamethylcyclopentasiloxane/dimethicone copolyol (sold under the name FA65DBF by Kobo) | 1.6 |
| Alumina-treated titanium oxide coated with perfluoroalkyl phosphate in decamethylcyclopentasiloxane/dimethicone copolyol (sold under the name FA65DF by Kobo) | 2.32 |
| Water | qs 100 |

The devices of examples 4 and 8 or 9 may be, for example, provided as a kit, associated with at least one item of information relating to a skin color, for example, a skin color similar to that of the user and/or to that desired by the user.

In Example 1, according to the proportion of covering composition, a more or less covering mixture is obtained. In Example 2, according to the proportion of the nacreous composition, a mixture that gives the skin more or less gloss is obtained. In Example 3, according to the proportion of the goniochromatic composition, a mixture in which the goniochromatic effect is more or less intense is obtained. In Example 4, a more or less colored mixture is obtained. Examples 5 to 8 differ from Examples 1 to 4 in the nature of the first composition. In Example 9, in addition to a variation in the color, a greater variation in the coverage than in the case of Example 8 is obtained.

Needless to say, the invention is not limited to examples described above.

The device may especially be configured to package and distribute three or more different compositions.

Throughout the description, including the claims, the term "comprising one" should be understood as being synonymous with the term "comprising at least one", unless otherwise specified, and "between" should be understood as being inclusive of the limits.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A process for preparing a cosmetic composition for the purpose of applying the composition to keratin material comprising mixing together at least a first cosmetic composition and a second cosmetic composition, which are different from each other and separately stored in a device for packaging and distributing the cosmetic composition, said device comprising a regulating member configured to allow a user to vary a relative proportion of at least one of said first and second cosmetic compositions the obtained mixture, the relative proportion conditioning at least one visible optical effect other than color in the mixture.

2. Process according to claim 1, wherein the second cosmetic composition is configured to produce the at least one optical effect with a variable degree as a function of a proportion thereof in the mixture.

3. Process according to claim 2, wherein the second cosmetic composition is configured to produce the at least one optical effect with varying degrees perceptible by the human eye as a function of a proportion thereof in the mixture.

4. Process according to claim 3, wherein the second cosmetic composition comprises particles that contribute toward the at least one optical effect in the mixture.

5. Process according to claim 4, wherein the first cosmetic composition is free of coloring agent and wherein the second cosmetic composition comprises a nacre.

6. Process according to claim 4, wherein the first cosmetic composition is free of coloring agent and wherein the second cosmetic composition comprises at least one coloring agent and a nacre.

7. Process according to claim 4, wherein the first cosmetic composition comprises a coloring agent and wherein the second cosmetic composition comprises at least one nacre.

8. Process according to claim 4, wherein the first cosmetic composition is free of coloring agent and wherein the second cosmetic composition comprises at least one filler and a coloring agent.

9. Process according to claim 4, wherein the first cosmetic composition comprises a coloring agent and wherein the second cosmetic composition comprises a filler.

10. Process according to claim 3, wherein the second cosmetic composition comprises a phase that contributes toward the at least one optical effect in the mixture.

11. Process according to claim 10, wherein the at least one optical effect comprises coverage.

12. Process according to claim 10, wherein the at least one optical effect comprises variation of color as a function of an angle of observation.

13. Process according to claim 12, wherein the second cosmetic composition comprises a goniochromatic coloring agent.

14. Process according to claim 13, wherein the goniochromatic coloring agent is selected from an interference multilayer structure and a liquid-crystal coloring agent.

15. Process according to claim 12, wherein the first cosmetic composition is free of coloring agent and wherein the second cosmetic composition comprises at least one goniochromatic coloring agent.

16. Process according to claim 15, wherein the first and second cosmetic compositions are distributed separately.

17. Process according to claim 10, wherein the at least one optical effect comprises diffraction of light.

18. Process according to claim 17, wherein the second cosmetic composition comprises a diffractive pigment.

19. Process according to claim 10, wherein the at least one optical effect comprises inhomogeneity of an appearance of the mixture.

20. Process according to claim 19, wherein the second cosmetic composition comprises reflective particles.

21. Process according to claim 19, wherein the second cosmetic composition comprises at least one of flakes and fibers that are visible to the naked eye.

22. Process according to claim 19, wherein the second cosmetic composition comprises an oily phase.

23. Process according to claim 10, wherein the at least one optical effect comprises gloss.

24. Process according to claim 23, wherein at least one of the first and second cosmetic compositions comprises a coloring agent.

25. Process according to claim 24, wherein the first cosmetic composition and the second cosmetic composition each comprise at least one coloring agent.

26. Process according to claim 25, wherein the first and second cosmetic compositions comprise a same coloring agent in different concentrations.

27. Process according to claim 25, wherein the first and second cosmetic compositions each comprise several pigments and wherein relative proportions of the pigments among each other are substantially equal between the first and second cosmetic compositions.

28. Process according to claim 24, wherein the coloring agent is selected from the group consisting of a mineral pigment, an organic pigment, an organic lake, a nacreous pigment, a composite pigment, a liposoluble dye, a water-soluble dye, and mixtures thereof.

29. Process according to claim 28, wherein the second cosmetic composition comprises at least one filler.

30. Process according to claim 29, wherein the filler is selected from the group consisting of talc, mica, silica, kaolin, sericite, polyamide powder, polyolefin powder, polyethylene powder, polytetrafluoroethylene powder, polymethyl methacrylate powder, polyurethane powder, starch powder, and silicone resin beads.

31. Process according to claim 1, wherein at least one of the first and second cosmetic compositions is free of coloring agent.

32. Process according to claim 1, wherein the first and second cosmetic compositions are free of UV-screening agent.

33. Process according to claim 1, wherein the device is configured to allow the first and second cosmetic compositions to be mixed inside the device.

34. Process according to claim 1, wherein the regulating member is rotary.

35. Process according to claim 1, wherein the regulating member comprises at least two positions corresponding to different relative proportions of the first cosmetic composition and the second cosmetic composition in the mixture.

36. Process according to claim 1, wherein the regulating member is configured to allow a user to distribute one of the first and second cosmetic compositions alone.

37. Process according to claim 1, wherein the regulating member is configured to allow a user to distribute the first cosmetic composition alone or the second cosmetic composition alone.

38. Process according to claim 1, wherein the regulating member is configured to allow continuous setting of a proportion of one of the first and second cosmetic compositions in the mixture.

39. Process according to claim 1, wherein the regulating member is configured to allow setting in increments of a proportion of one of the first and second cosmetic compositions in the mixture.

40. Process according to claim 1, wherein the device is configured to simultaneously distribute the first and second cosmetic compositions.

41. Process according to claim 1, wherein the regulating member comprises at least two successive regulating positions and wherein a variation in color of the mixture between the two successive positions is not greater than about 0.8.

42. Process according to claim 41, wherein a course between two successive positions represents less than a quarter of a total course of the regulating member.

43. Process according to claim 1, wherein a variation in color of the mixture between two extreme positions of the regulating member is not greater than about 2.

44. Process according to claim 1, wherein the device is configured to deliver at least one item of information concerning the relative proportion of the first and second cosmetic compositions in the mixture as a function of a setting selected by a user.

45. Process according to claim 1, wherein the device is configured to give at least one item of information regarding at least one optical property of the mixture as a function of a setting selected by a user.

46. Process according to claim 45, wherein the device is not provided with an applicator for application of the mixture.

47. Process according to claim 46, wherein the device comprises at least one pump for distributing at least one of the first and second cosmetic compositions and the mixture.

48. Process according to claim 1, wherein the device comprises an applicator for applying the mixture.

49. Process according to claim 48, wherein the applicator comprises an at least partially elastically deformable structure.

50. Process according to claim 1, wherein at least one of the first and second cosmetic compositions is contained in a removable container of the device.

51. Process according to claim 50, wherein the device is combined with a plurality of different compositions that may be used as the first cosmetic composition.

52. Process according to claim 50, wherein the device is combined with a plurality of different compositions that may be used as the second cosmetic composition.

53. Process for making up a keratin material, comprising:
applying to the keratin material a mixture prepared by mixing together at least a first cosmetic composition and a second cosmetic composition, which are different from each other and separately stored in a device for packaging and distributing the cosmetic composition, said device comprising a regulating member configured to allow a user to vary a relative proportion of at least one of said first and second cosmetic compositions in the obtained mixture, the relative proportion conditioning at least one visible optical effect other than color in the mixture.

54. Process according to claim 53, comprising:
setting the regulating member to a first setting;
making up a first area of the keratin material with the mixture according to the first setting;
setting the regulating member to a second setting different from the first setting; and
making up a second area of the keratin material with the mixture according to the second setting.

55. Process according to claim 53, comprising:
choosing a visual result;
setting the regulating member to a setting aimed at obtaining the chosen visual result; and
making up an area of at least one of skin, lips and integuments with the mixture according to the setting.

56. Process according to claim 53, wherein the mixture is applied to the skin, the lips, or the nails.

* * * * *